US008126238B2

(12) United States Patent
Skinner et al.

(10) Patent No.: US 8,126,238 B2
(45) Date of Patent: Feb. 28, 2012

(54) METHOD AND SYSTEM FOR AUTOMATICALLY IDENTIFYING AND DISPLAYING VESSEL PLAQUE VIEWS

(75) Inventors: John V. Skinner, New Berlin, WI (US); Gopal B. Avinash, New Berlin, WI (US); Saad Ahmed Sirohey, Pewaukee, WI (US); Sandeep Dutta, Waukesha, WI (US); Patricia Le Nezet, Le Pecq (FR); Deann Marie Haas, Port Washington, WI (US)

(73) Assignee: General Electric Company, Schenectady, NY (US)

( * ) Notice: Subject to any disclaimer, the term of this patent is extended or adjusted under 35 U.S.C. 154(b) by 1498 days.

(21) Appl. No.: 11/603,488

(22) Filed: Nov. 22, 2006

(65) Prior Publication Data

US 2008/0118131 A1 May 22, 2008

(51) Int. Cl.
*G06K 9/00* (2006.01)

(52) U.S. Cl. .......... 382/131

(58) Field of Classification Search .......... 378/1, 37, 378/21, 41, 42, 38, 44, 51, 62, 65, 146; 382/100, 382/128, 129, 130, 131, 132, 133, 134, 173, 382/181; 128/920; 600/300, 407

See application file for complete search history.

(56) References Cited

U.S. PATENT DOCUMENTS 6,331,116 B1 12/2001 Kaufman et al.
6,477,401 B1 11/2002 Johnson et al.
6,603,494 B1 8/2003 Banks et al.
6,925,200 B2 8/2005 Wood et al.
6,947,784 B2 9/2005 Zalis
7,027,630 B2 4/2006 Bruijns
7,072,501 B2 7/2006 Wood et al.
7,123,760 B2 10/2006 Mullick et al.
2003/0007598 A1* 1/2003 Wang et al. .......... 378/37
2004/0066958 A1* 4/2004 Chen et al. .......... 382/128
2004/0249270 A1* 12/2004 Kondo et al. .......... 600/425
2005/0094858 A1 5/2005 Sirohey et al.
2005/0147297 A1 7/2005 McLaughlin et al.
2005/0259854 A1 11/2005 Arimura et al.
2006/0064396 A1* 3/2006 Wei et al. .......... 707/1

(Continued)

FOREIGN PATENT DOCUMENTS

WO WO 2005/023086 A2 * 3/2005

(Continued)

OTHER PUBLICATIONS

Faber et al., "Three-Dimensional Fusion of Coronary Arteries with Myocardial Perfusion Distributions: Clinical Validation", Journal of Nuclear Medicine, vol. 45 No. 5 745-753, 2004.*

(Continued)

*Primary Examiner* — Bhavesh Mehta
*Assistant Examiner* — Tahmina Ansari
(74) *Attorney, Agent, or Firm* — The Small Patent Law Group; Dean D. Small

(57) ABSTRACT

A method for processing computed tomography (CT) datasets comprises identifying regions of interest (ROIs) within a CT dataset is provided. The ROIs are ranked based on a comparison to at least one predetermined parameter. The ranking determines a level of importance for the ROIs with respect to each other. A list of the ROIs is provided on a display, the list indicating the ROIs based on an associated level of importance. The ROIs are selectable with a user interface.

21 Claims, 5 Drawing Sheets

U.S. PATENT DOCUMENTS

| | | | | |
|---|---|---|---|---|
| 2006/0079743 | A1 | 4/2006 | Ferrant et al. | |
| 2006/0215896 | A1 | 9/2006 | Sirohey et al. | |
| 2006/0241427 | A1 * | 10/2006 | Kinouchi et al. | 600/437 |
| 2007/0019846 | A1 * | 1/2007 | Bullitt et al. | 382/128 |
| 2007/0019850 | A1 * | 1/2007 | Knoplioch et al. | 382/131 |
| 2009/0005693 | A1 * | 1/2009 | Brauner et al. | 600/481 |
| 2009/0279752 | A1 * | 11/2009 | Sirohey et al. | 382/128 |

FOREIGN PATENT DOCUMENTS

WO WO 2006069379 A2 * 6/2006

OTHER PUBLICATIONS

Eberl. et al., "BI-RADS Classification for Management of Abnormal Mammograms", Mar.-Apr. 2006, J. Am Board Fam Med 2006; 19:161-4, availalble online at http://www.jabfm.org.*

Laurent Saroul, Oscar Figueiredo, and Roger D. Hersch. Distance Preserving Flattening of Surface Sections, IEEE Transactions on Visualization and Computer Graphics, vol. 12, No. 1, Jan.-Feb. 2006, 10 pgs.

Hirai et al., Intracranial Aneurysms at MR Angiography: Effect of Computer-aided diag on Radiologists Det. Perf., Radiology 2005; 237:605-610, RSNA 2005.

Doi, Current status and future potential of computer-aided diagnosis in medical imaging, British Journal of Radiology (2005) 78, S3-s19.

Cai et al., Special session on colon liver and Brain CAD, Int J CARS (2006) 1:369-388.

Hisanori et al., Development of cerebral aneurysm computer-aided detection systems with 3D mra data, Yokogawa Technical Report English Edition, No. 39 (2005).

Kobashi et al., Computer-aided diagnosis of intracranial aneurysms in MRA images with case-based reasoning, IEICE Transactions on Information and Systems 2006 E89-D(1):340-350.

Ninomiya et al., Feature Extraction from MRA Images for Fuzzy Rule-based Diagnosis of Cerebral Aneurysms, http://scholar.google.com/scholar?hl=en&lr=&q=cache:zcJ5_ZuD34oJ:wwwj3.comp.eng.himeji-tech.as.jp/staff/kobashi/reprints/SCIS2002-ninomiya.pdf.

Uchiyama et al., Computer-aided diagnosis scheme for detection of unruptured intracranial aneurysms in MR angiography, Eng in Med and Bio Society, 2005; IEEE-EMBS 20.

Saad Sirohey; "Lung VCAR"; General Electric Company; 6 pages.

Lichan Hong; "Virtual voyage; Interactive Navigation in the Human Colon"; Center for visual Computing State university of New york at Stony Brook; 8 pages.

* cited by examiner

METHOD AND SYSTEM FOR AUTOMATICALLY IDENTIFYING AND DISPLAYING VESSEL PLAQUE VIEWS

BACKGROUND OF THE INVENTION

This invention relates generally to processing computer tomography (CT) datasets, and more particularly, to determining optimal views of structures such as plaque deposits within vessels.

Cardiovascular related deaths constitute more than 500,000 people annually in the USA, and much more globally. A major portion of the deaths are attributed to coronary artery disease, where the chief culprit is the build up of plaque, such as soft plaque and its ruptures, as well as hard plaque or calcification.

Plaque deposits are analyzed for size, location and composition, for example. Coronary plaque has been classified into six stages according to the Stary scale. According to general consensus, it is crucial to determine the plaque in stages 4 and 5. At this level, the plaque constitutes critical vulnerable plaque and could lead to rupture or dislodging of the plaque, causing blockages and leading to myocardial infarction.

Newer scanning technologies, such as Volume Computed Tomography (VCT) and associated increases in spatial and temporal resolution have made it possible to image a contrasted study of the heart which is gated to mitigate heart motion. Using these images, it is possible to distinguish soft plaque from lumen (the vessel wall) and from calcification. However, the regions of interest (ROIs) within which the plaque deposits are located are small, and determining the desired orientation of the ROI to best view the deposit or other structure of interest within the vessel is time consuming. Also, many plaque deposits may be present, and navigating through the image dataset to review all or the majority of the deposits to identify the most vulnerable may require substantial time and resources.

Therefore, a need exists for automating aspects of locating and displaying deposits within the vessels. Certain embodiments of the present invention are intended to meet these needs and other objectives that will become apparent from the description and drawings set forth below.

BRIEF DESCRIPTION OF THE INVENTION

In one embodiment, a method for processing computed tomography (CT) datasets comprises identifying regions of interest (ROIs) within a CT dataset. The ROIs are ranked based on a comparison to at least one predetermined parameter. The ranking determines a level of importance for the ROIs with respect to each other. A list of the ROIs is provided on a display, the list indicating the ROIs based on an associated level of importance. The ROIs are selectable with a user interface.

In another embodiment, a system for processing images comprises a processor identifying ROIs comprising image data within a diagnostic dataset. A prioritizing module is coupled to the processor for creating a prioritized list of the ROIs based on a vulnerability score associated with each of the ROIs. An optimal view module is coupled to the processor and the prioritizing module for determining an optimal viewing angle for each of the ROIs based on the image data within the ROI.

In another embodiment, a method for processing images comprises identifying ROIs comprising image data within a diagnostic dataset. A prioritized list of the ROIs is formed based on a vulnerability score associated with each of the ROIs. An optimal viewing angle is determined for each of the ROIs based on the image data within the ROI.

DETAILED DESCRIPTION OF THE INVENTION

Figure 1:
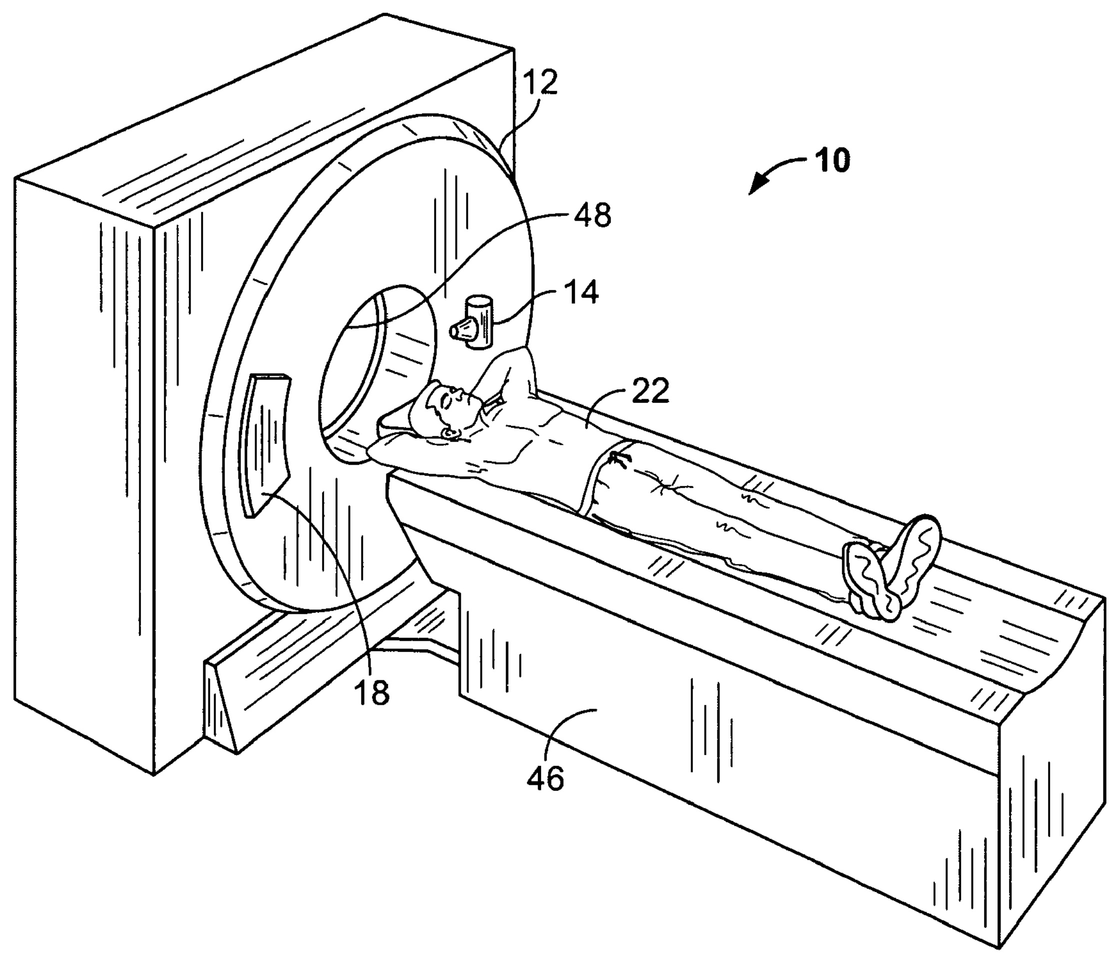
FIG. 1 illustrates a pictorial view of a computed tomography (CT) imaging system in accordance with an embodiment of the present invention.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

Figure 2:
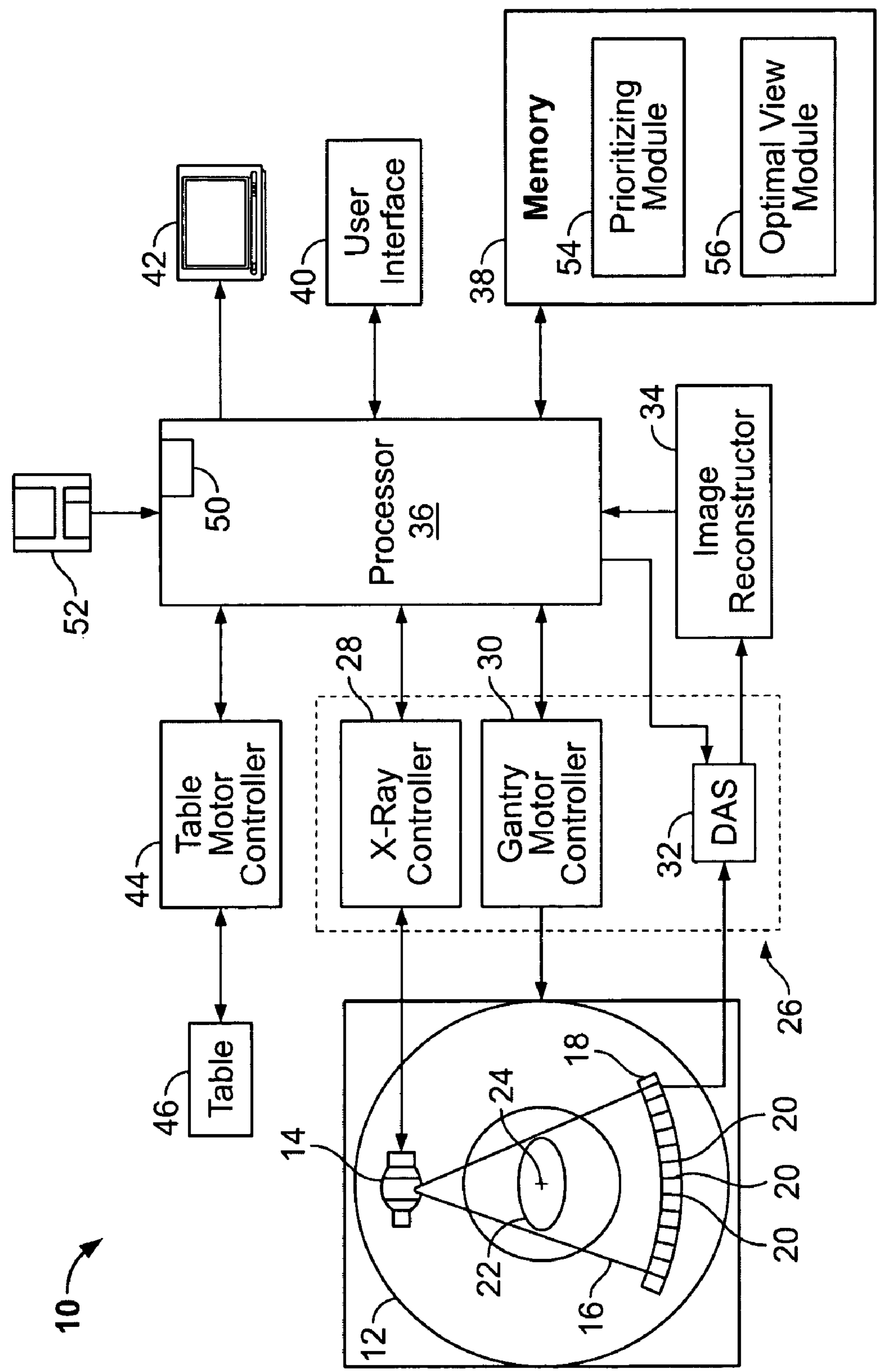
FIG. 2 illustrates a block diagram of the system of FIG. 1 in accordance with an embodiment of the present invention.

FIG. 1 illustrates a pictorial view of a computed tomography (CT) imaging system 10. The system 10 includes a gantry 12 representative of a "third generation" CT imaging system. FIG. 2 illustrates a block diagram of the system 10 of FIG. 1, and will be discussed together with FIG. 1.

The gantry 12 has an x-ray source 14 that projects a beam of x-rays 16 toward a detector array 18 on the opposite side of the gantry 12. The detector array 18 is formed by a plurality of detector rows (not shown) including a plurality of detector elements 20 which together sense the projected x-rays that pass through an object, such as a medical patient 22. Each detector element 20 produces an electrical signal that represents the intensity of an impinging x-ray beam and hence the attenuation of the beam as it passes through the patient 22. During a scan to acquire x-ray projection data, the gantry 12 and the components mounted thereon rotate about a center of rotation 24. FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan.

Rotation of the gantry 12 and the operation of the x-ray source 14 are governed by a control mechanism 26 of the CT system 10. The control mechanism 26 includes an x-ray controller 28 that provides power and timing signals to the x-ray source 14 and a gantry motor controller 30 that controls the rotational speed and position of the gantry 12. A data acquisition system (DAS) 32 in the control mechanism 26 samples analog data from the detector elements 20 and converts the data to digital signals for subsequent processing. An image reconstructor 34 receives sampled and digitized x-ray data from the DAS 32 and performs high-speed image reconstruction. The reconstructed image is applied as an input to a processor 36 which stores the image in memory 38.

The processor 36 also receives commands and scanning parameters from an operator via user interface 40 that has input devices such as a keyboard, mouse, trackball and the like. An associated display 42 allows the operator to observe the reconstructed image and other data from the processor 36. Optionally, operator input may be provided through a touch screen monitor. The operator supplied commands and parameters are used by the processor 36 to provide control signals and information to the DAS 32, x-ray controller 28, and gantry motor controller 30. In addition, the processor 36 operates a table motor controller 44 which controls a motorized table 46 to position the patient 22 with respect to the gantry 12. Particularly, the table 46 moves portions of the patient 22 through gantry opening 48.

In one embodiment, the processor 36 includes a device 50, for example, a floppy disk drive or CD-ROM drive, for reading instructions and/or data from a computer-readable medium 52, such as a floppy disk or CD-ROM. In another embodiment, the processor 36 executes instructions stored in firmware (not shown). The processor 36 is programmed to perform functions described herein, and as used herein, the term processor is not limited to just those integrated circuits referred to in the art as processors, but broadly refers to computers, processors, microcontrollers, microcomputers, programmable logic controllers, application specific integrated circuits, and other programmable circuits, and these terms are used interchangeably herein.

A prioritizing module 54 is provided within the memory 38 for determining a prioritized list of lesions or regions of interest based on desired parameters within a CT dataset. The prioritized list is selectable, such as a list of bookmarks, which may be prioritized or ranked based on factors such as vulnerability, percentage of occlusion, extent of a lesion from a vessel wall, as well as other factors. When the user selects a bookmark, an optimal view module 56 automatically computes an optimal view for the indicated data.

Also, it should be understood that the processor 36, memory 38, user interface 40, and display 42 and may be provided separate from the system 10 for processing data. The acquired CT datasets may be transferred over a network, internet, by portable disk, and the like, for processing at a location remote from the system 10.

Figure 3:
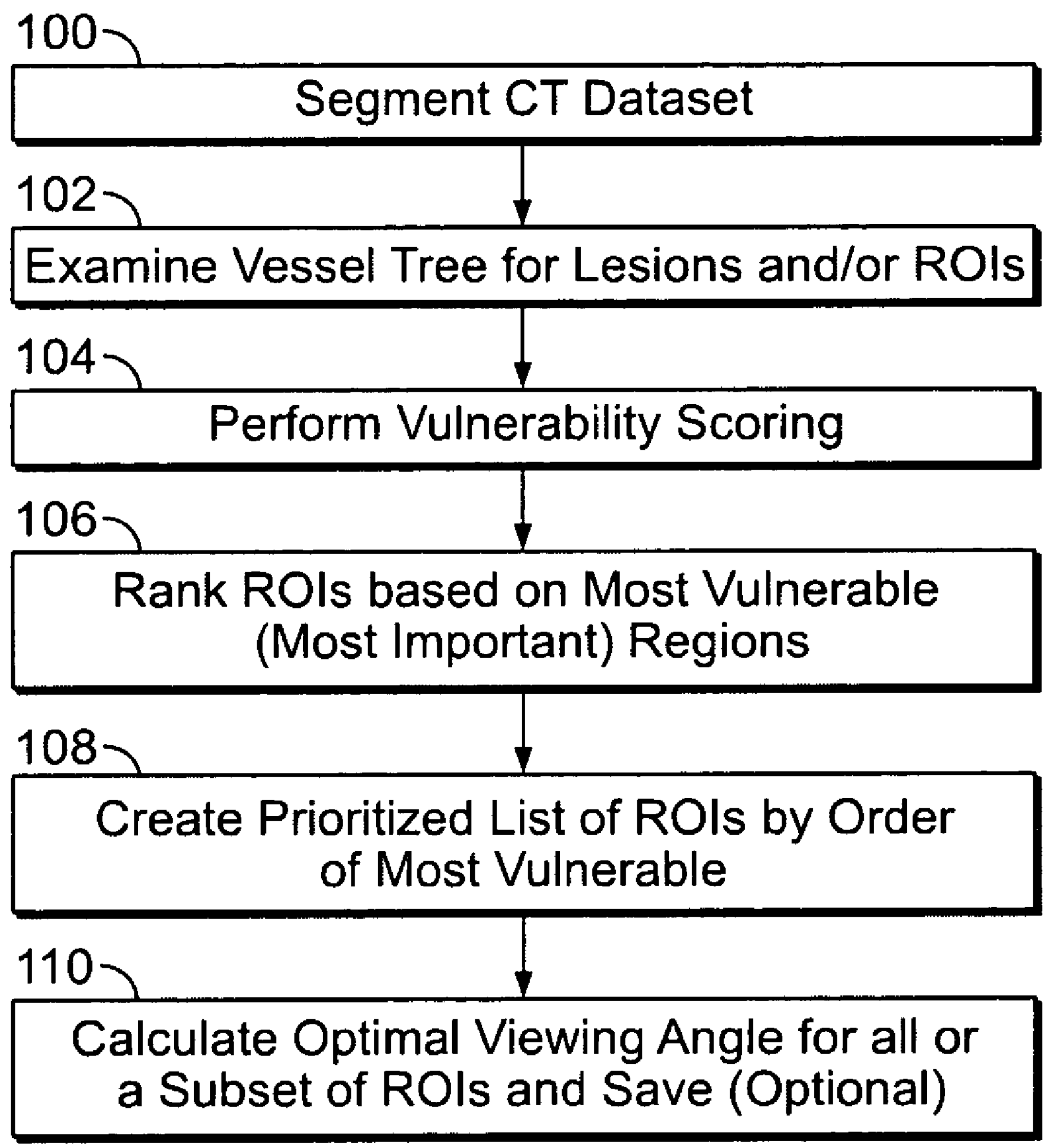
FIG. 3 illustrates a method for automatically creating a prioritized list of regions of interest (ROIs) within a CT dataset in accordance with an embodiment of the present invention.

FIG. 3 illustrates a method for automatically creating a prioritized list of regions of interest (ROIs) within a CT dataset. At 100, the processor 36 segments the CT dataset to locate the complete coronary vessel tree. Alternatively, other anatomy may be imaged, such as peripheral vasculature within limbs and carotid vessel tree. Although CT datasets are discussed, the prioritization may also be applied to segmented datasets acquired with other modalities.

At 102, the processor 36 defines the ROIs within the vessel tree. An analysis of the CT dataset may be accomplished to automatically detect lesions such as hard and soft plaque deposits. The ROIs may then be based on the data within the CT dataset, such as by the size of a deposit, composition of a deposit, and the presence of more than one deposit within a predetermined area or separated by a predetermined distance. ROIs may also be predetermined, such as by automatically dividing the segmented vessel tree into areas based on vessel branches, a predetermined maximum or minimum size of ROI, user defined vessels of interest, and the like.

At 104, the processor 36 performs a vulnerability scoring by comparing the ROIs to at least one predetermined parameter. The vulnerability scoring may take one or more factors into consideration to determine whether the deposit exhibits a low, medium, or high level of risk to the patient 22, such as by dislocation or occlusion based on size, location, or composition. The predetermined parameters may be a location of a deposit with respect to other anatomical landmarks, a size or volume of a deposit, extent or peak distance of a deposit from the vessel surface, a composition of a deposit, location of a deposit with respect to a branching vessel, movement of the tissue proximate to a deposit, intensity of voxels within the ROI, and the like. For calcium or hard plaque deposits, a vulnerability score may be determined which is an aggregation of hounsfield numbers for the plaque deposits, then compared to a predetermined score that provides an indication of risk.

At 106, the prioritizing module 54 performs a ranking of the ROIs based on at least the vulnerability score determined at 104. The ROIs may be ranked from most vulnerable, the lesion and/or ROI which presents the highest potential risk to the patient 22, to the least vulnerable. Within a single CT dataset, there may be many detected ROIs which previously provided an overwhelming amount of data for the user to analyze. By ranking the ROIs, the user can review the most vulnerable lesions first rather than searching for the most vulnerable lesions and manually ranking the lesions. Optionally, the prioritizing module 54 may identify a sub-set of the ROIs reflecting the ROIs which are the most vulnerable. The number of ROIs within the sub-set may be predetermined or based on a percentage of the total number of ROIs detected, for example. Optionally, the prioritizing module 54 may organize the ROIs into a plurality of sub-groups based on vulnerability scoring, such as into three sub-groups. All of the ROIs within a sub-group may be assigned the same number and/or a display color or other indicator to indicate level of vulnerability.

At 108, the prioritizing module 54 creates a prioritized list of ROIs by order of vulnerability or based on an associated level of importance. The prioritized list may also provide cross-reference data to anatomical information within an anatomical atlas, and may define the vessel and/or anatomical location of the ROI. The prioritized list is used to provide an interface through which the user can easily select and view particular ROIs.

Optionally, at 110 the optimal view module 56 may calculate optimal viewing angles for all or a sub-set, if identified, of the ROIs, which is discussed further below. The calculated optimal viewing angles may then be saved in the digital file associated with the patient 22 in the memory 38. The optimal viewing angles may later be quickly retrieved and an optimal view displayed as discussed below.

Figure 4:
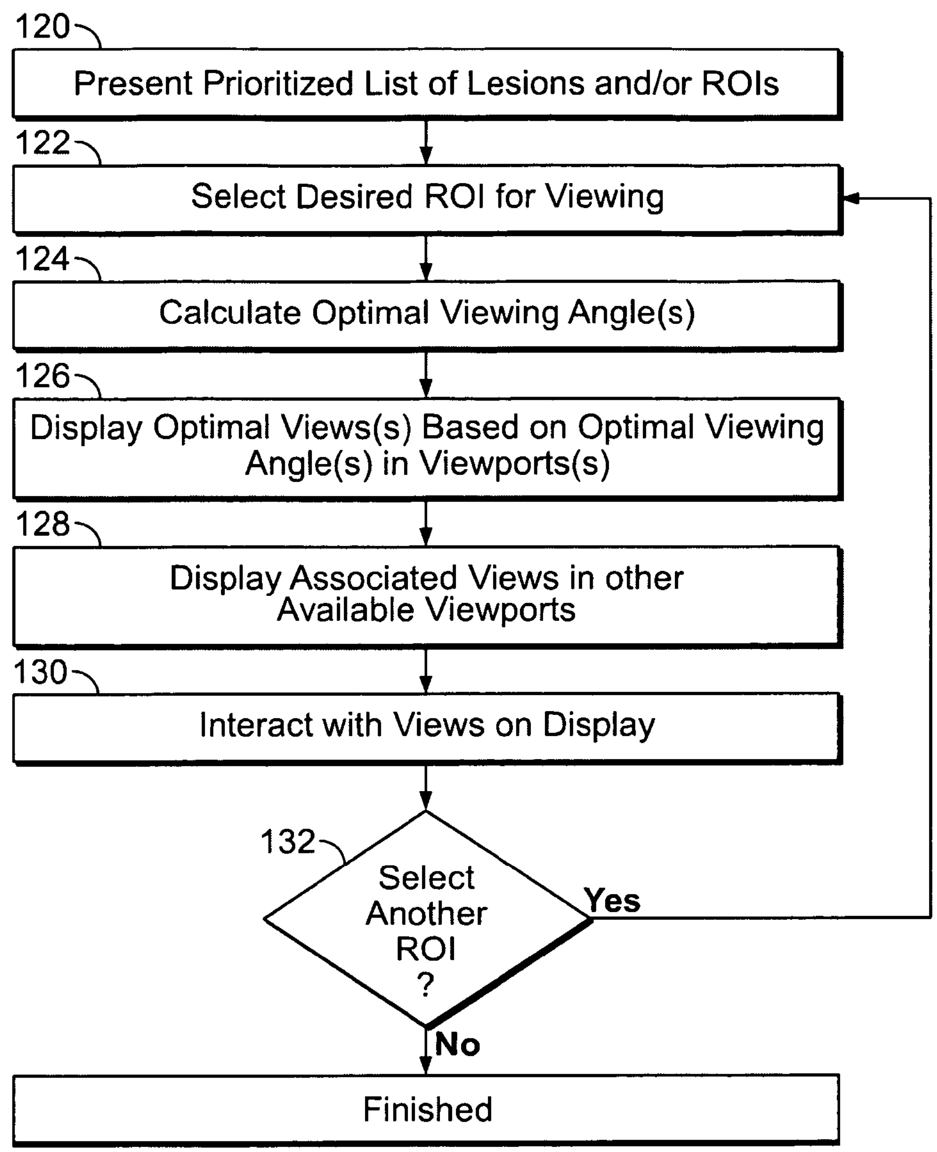
FIG. 4 illustrates a method for automatically calculating optimal viewing angles of lesions for display in accordance with an embodiment of the present invention.

FIG. 4 illustrates a method for automatically calculating optimal viewing angles of lesions for display. An optimal viewing angle may be based on the context of the image data within the ROI, and is typically unique for each ROI. It can be time consuming for the user to move through the image data to find the optimal viewing angle. By automatically presenting an optimal view based on the optimal viewing angle, the user may quickly evaluate the image and make desired calculations and measurements.

Figure 5:
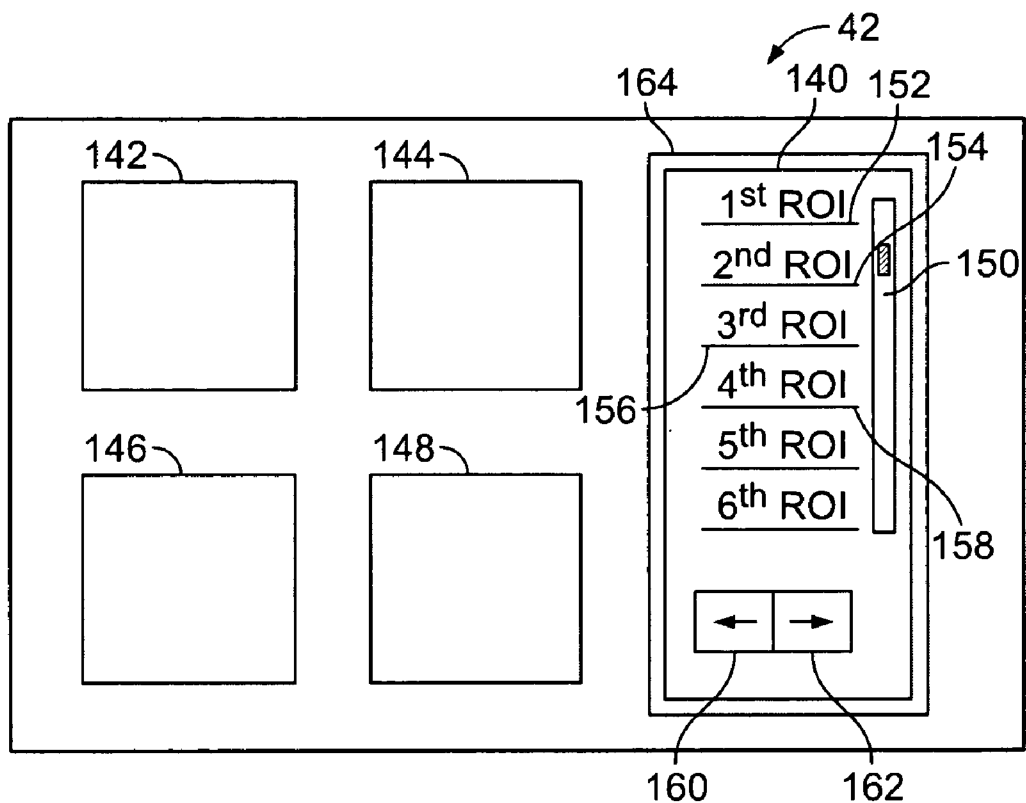
FIG. 5 illustrates a display with an interface for displaying the prioritized list of ROIs and multiple viewports in accordance with an embodiment of the present invention.

At 120, the prioritizing module 54 presents at least a portion of the prioritized list of ROIs or lesions to the user on the display 42. FIG. 5 illustrates the display 42 with an interface 164 displaying the prioritized list of ROIs and first, second, third through N viewports 142, 144, 146 and 148 indicated. The interface 164 may be any graphical user interface providing the ability for the user to interact with the prioritized list of ROIs. In this example, the interface 164 displays a bookmarked list 140.

The bookmarked list 140 may be displayed anywhere on the display 42, and may be a variety of sizes. The bookmarks within the bookmarked list 140 may be "live" wherein the user may directly select one with the user interface 40, such as by clicking on the text with a mouse or touching the text if the display 42 is a touchscreen. Alternatively, a selection may be made using voice commands. The user may drag the bookmarked list 140 to a different position using the user interface 40, change the size of the display window, and scroll through the ROIs and lesions displayed on the bookmarked list 140 by using scroll bar 150. Optionally, arrows 160 and 162, or other indicators, may be provided to step backwards and forwards, respectively, to sequence through the bookmarked list 140.

Alternatively, the bookmarked list 140 may be presented in any other user interface format or combinations of formats, such as a pull-down menu, individual tabs, presented graphically on a 3D model, and displayed on a second monitor separate from the display 42. The bookmarks within the bookmarked list 140 may also be presented in sub-groups based on anatomical location or vulnerability. Each of the bookmarks may be displayed with a ranking number or color indicating an associated level of priority.

At 122 of FIG. 4, the user selects an ROI with the user interface 40, such as first ROI 152. At 124, the optimal view module 56 calculates at least one key or optimal viewing angle for displaying the first ROI 152. The optimal viewing angle is determined based on the context of the image data within the first ROI 152, and reflects a plane which intersects through an ideal point of the lesion or other anatomy within the first ROI 152. The optimal view module 56 may analyze potential views having different angles through the first ROI 152 to determine the optimal viewing angle. The optimal viewing angle may be based on a desired display of one or more of a type of lesion within the first ROI 152, an ideal point or plane indicating a peak or highest point of a plaque deposit, a plane having a maximum amount of occlusion within a vessel, and a largest cross-section of a branching vessel.

More than one key view may be desired based on the lesion and anatomy within an ROI. For example, if the ROI comprises a branching vessel, the optimal view module 56 may calculate a first optimal viewing angle to display the largest cross-section of the branching vessel and a second optimal viewing angle to display the peak of a plaque deposit. Also, if more than one plaque deposit is present within an ROI, the optimal view module 56 may calculate optimal viewing angles for each of the plaque deposits.

At 126, the processor 36 displays at least one optimal view based on the at least one optimal view angle in at least one viewport on the display 42. The optimal view may be a reformat or volume rendering view, for example, which is optimized locally rather than globally. For example, the optimal view may be a reformat view which is a geometrically true representation of the anatomical data. Therefore, the user may easily perform measurements and calculations on the reformat view. For example, in FIG. 5 the user may select the first ROI 152 from the bookmarked list 140, the optimal view module 56 calculates the optimal viewing angle for displaying the lesion within the first ROI 152, and then the processor 36 displays the optimal view based on the optimal viewing angle in the first viewport 142.

Figure 6:
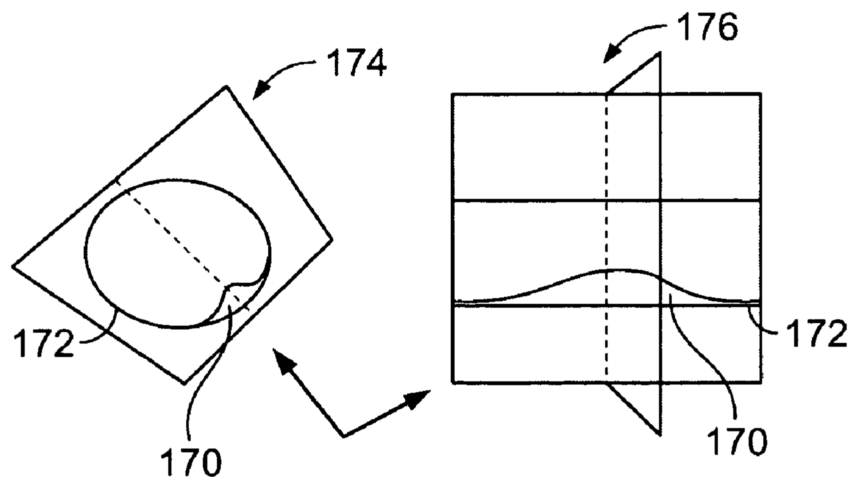
FIG. 6 illustrates optimized views of an ROI having a lesion, such as a plaque deposit, within a vessel in accordance with an embodiment of the present invention.

FIG. 6 illustrates optimized views of an ROI having a lesion, such as a plaque deposit 170, within a vessel 172. The optimal view module 56 calculates an optimal viewing angle based on a maximum height or peak of the plaque deposit 170, which is a point of greatest displacement of the plaque with respect to the vessel wall. Alternatively, if the optimal view module 56 previously calculated the optimal viewing angle (such as at 110 of FIG. 3), the optimal view module 56 may retrieve the optimal viewing angle from the memory 38. The processor 36 may display first and/or second optimal views 174 and 176 based on the optimal viewing angle which are two different cross-reference views through the peak of the plaque deposit 170. The first and second optimal views 174 and 176 may be reformat views and displayed in the first and second viewports 142 and 144 of the display 42 (FIG. 5), for example.

Figure 7:
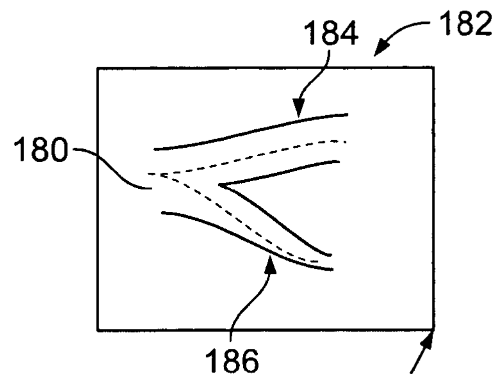
FIG. 7 illustrates an optimized view of another ROI having a vessel branching point with first and second branching vessels in accordance with an embodiment of the present invention.

FIG. 7 illustrates an optimized view of a different ROI having a vessel branching point 180 with first and second branching vessels 184 and 186. The optimal view module 56 calculates an optimal viewing angle based on the widest or largest cross-section of the first and second branching vessels 184 and 186, which may be based on a least squares condition. The processor 36 then displays optimal view 182, which in this example is a least squares reformat plane. Alternatively, the optimal viewing angle may be based on the greatest distance between the vessel walls of at least one of the first and second branching vessels 184 and 186. Alternatively, the optimal view module 56 may also consider topological placement of deposits (not shown) with reference to other anatomical locations within the branching vessel.

At 128 of FIG. 4, the processor 36 displays associated views in one or more other viewports on the display 42. Each displayed view may have a common 3D cursor providing synchronized viewing, as well as a global reference for all displayed views. The associated views may be any typically available view or traditional view, and may be globally optimized. For example, one or more of a global image, a planar image, a geometrically accurate image and a 3D image may be displayed.

At 130, the user may interact with the optimal view, as well as the other associated views, to measure parameters, perform calculations, and/or change the optimal viewing angle of the optimal view with the user interface 40. For example, location, size and composition of plaque deposits can be measured and analyzed, as well as parameters associated with blood flow, diameter and restrictions within the vessel. The user may also save data, input data, record findings and recommendations, and the like. The saved data may be linked to the ROI being displayed for future reference, printing and viewing.

At 132, if the user wishes to select another ROI or lesion for viewing, the method returns to 122. Otherwise, the method is finished. If another ROI or lesion is selected, the first through fourth viewports 142-148 are all updated with data related to the currently selected ROI.

In another embodiment, the optimal view module 56 may calculate one or more optimal view angles automatically, such as for the first ROI 152, second ROI 154, third ROI 156, and fourth ROI 158, which have been determined to be the most vulnerable. The processor 36 may then automatically display the optimal views associated with the first through fourth ROIs 152-158 within the first through fourth viewports 142-148, respectively.

A technical effect is automatically determining a prioritized list of lesions and/or ROIs within a vessel tree of a segmented CT dataset. The ROIs have plaque deposits within vessels or other structures of interest. The prioritized list may organize the list of ROIs based on vulnerability to lesion dislocation or other critical concern to the patient 22. An optimal viewing angle is automatically calculated for each of the ROIs based on context of the image data and other predetermined parameters to provide an optimal view of the deposit or other structure on a display.

While the invention has been described in terms of various specific embodiments, those skilled in the art will recognize that the invention can be practiced with modification within the spirit and scope of the claims.

What is claimed is:

1. A method for processing computed tomography (CT) datasets, comprising:

identifying regions of interest (ROIs) within a CT dataset, wherein the ROIs include abnormalities in a blood vessel of a patient and an anatomy indicating a plaque deposit within a vessel;

comparing the ROIs to at least one predetermined parameter;

determining a level of diagnostic importance for the ROIs with respect to each other based on the comparison, the level of diagnostic importance related to a risk associated with the abnormalities;

ranking the ROIs based on the level of diagnostic importance;

providing a list of the ROIs on a display, the list indicating the level of diagnostic importance of the ROIs, the ROIs being selectable within a user interface;

identifying a cross-sectional view indicating a greatest displacement of the plaque deposit with respect to the vessel wall; and displaying the cross-sectional view.

2. The method of claim 1, further comprising displaying at least one image based on a selected ROI from the list as a result of a selection made within the user interface.

3. The method of claim 1, further comprising displaying at least one geometrically accurate image based on a selected ROI from the list as a result of a selection made within the user interface.

4. The method of claim 1, further comprising:

displaying at least one geometrically accurate image based on a selected ROI from the list as a result of a selection made with the user interface; and displaying at least a second image representative of a global representation based on the selected ROI.

5. The method of claim 1, wherein the ROIs comprise anatomy indicating at least one of vessels and plaque within the vessels, the ranking being based on a vulnerability associated with the plaque.

6. The method of claim 1, wherein the list further comprises at least one of a bookmarked list, links displayed within a window, a pull-down menu, arrows, an anatomical model, and tabs.

7. The method of claim 1, further comprising:

indicating a selected ROI based on an input from the user interface.

8. The method of claim 1, further comprising:

indicating a selected ROI based on an input from the user interface, the selected ROI comprising anatomy indicating a vessel branching point having at least first and second branching vessels;

identifying an optimal viewing angle within the selected ROI indicating a greatest distance between vessel walls of at least one of the first and second branching vessels; and displaying an optimal view based on the optimal viewing angle, the optimal view displaying a geometrically accurate representation of the selected ROI.

9. A system for processing images, comprising:

a processor identifying regions of interest (ROIs) comprising image data within a diagnostic dataset, wherein the ROIs include abnormalities in a blood vessel of a patient and an anatomy indicating a plaque deposit within a vessel;

the processor also identifying a cross-sectional view indicating a greatest displacement of the plaque deposit with respect to the vessel wall;

a prioritizing module coupled to the processor, the prioritizing module determining a vulnerability score of each of the ROIs, the prioritizing module creating a prioritized list of the ROIs based on the vulnerability score of each of the ROIs, the vulnerability score related to a risk associated with the abnormalities;

a optimal view module coupled to the processor and the prioritizing module, the optimal view module determining an optimal viewing angle for each of the ROIs based on the image data within the ROI; and a display module for displaying the optimal viewing angle for each of the ROIs, wherein the optimal viewing angle includes the cross-sectional view.

10. The system of claim 9, further comprising a display coupled to the processor for displaying an optimal view based on the optimal viewing angle, the optimal view providing a geometrically accurate representation of the image data within an ROI.

11. The system of claim 9, further comprising:

a display coupled to the processor, the display displaying the prioritized list of the ROIs; and a user interface for selecting an ROI from the prioritized list, the display displaying at least one view based on the ROI.

12. The system of claim 9, wherein the image data further comprises anatomy indicating at least one of vessels and plaque within the vessels, the vulnerability score being based on at least one of a vulnerability associated with the plaque and a location of the plaque relative to surrounding anatomy within the diagnostic dataset.

13. A method for processing images, comprising:

identifying regions of interest (ROIs) comprising image data within a diagnostic dataset, wherein the ROIs include abnormalities in a blood vessel of a patient and an anatomy indicating a plaque deposit within a vessel;

determining a vulnerability score of each of the ROIs, the vulnerability score related to a risk associated with the abnormalities;

identifying a cross-sectional view indicating a greatest displacement of the plaque deposit with respect to the vessel wall;

forming a prioritized list of the ROIs based on a vulnerability score associated with each of the ROIs;

determining an optimal viewing angle for each of the ROIs based on the image data within the ROI, wherein the optimal viewing angle includes the cross-sectional view.

14. The method of claim 13, further comprising:

bookmarking the prioritized list; and displaying at least a portion of the prioritized list, each of the ROIs within the prioritized list being selectable with a user interface.

15. The method of claim 13, wherein the image data comprises at least a vessel and a plaque deposit within the vessel, the vulnerability scores being based on a potential of the plaque deposit to dislocate from the vessel wall.

16. The method of claim 13, wherein the image data comprises at least a vessel and a plaque deposit within the vessel, the optimal viewing angle being based on a greatest displacement of the plaque deposit from a vessel wall of the vessel.

17. The method of claim 13, wherein the image data comprises at least a vessel and a plaque deposit within the vessel, the optimal viewing angle being based on a maximum amount of occlusion within the vessel.

18. The method of claim 13, wherein the image data comprises a vessel branching point having at least first and second branching vessels, the optimal viewing angle being based on a greatest distance between vessel walls of at least one of the first and second branching vessels.

19. The method of claim 13, wherein the image data comprises a vessel branching point having first and second branching vessels, the optimal viewing angle indicating a greatest distance between vessel walls of both of the first and second branching vessels.

20. The method of claim 13, further comprising:

accepting an input from the user interface indicating a selected ROI from the prioritized list;

displaying a geometrically accurate representation of the selected ROI based on the optimal viewing angle; and displaying at least a second image based on the selected ROI, the second image being one of a global image, a planar image, a geometrically accurate image, and a 3D image.

21. The method of claim 1, wherein the abnormalities include plaque deposits in the blood vessel of the patient.

* * * * *